United States Patent
Shekhar

(12) 
(10) Patent No.: US 6,564,091 B2
(45) Date of Patent: May 13, 2003

(54) METHOD AND MEMORY MEANS FOR STORING CARDIAC RHYTHM INFORMATION

(75) Inventor: Mrigank Shekhar, Vancouver, WA (US)

(73) Assignee: Biotronik Mess-und Therapiegerate GmbH & Co. Ingenieurburo Berlin, Berlin (DE)

(*) Notice: Subject to any disclaimer, the term of this patent is extended or adjusted under 35 U.S.C. 154(b) by 0 days.

(21) Appl. No.: 09/862,082

(22) Filed: May 22, 2001

(65) Prior Publication Data

US 2002/0177784 A1 Nov. 28, 2002

(51) Int. Cl.[7] .............................................. A61B 5/0452
(52) U.S. Cl. ............................................ 600/516; 607/9
(58) Field of Search ............................... 600/509, 510, 600/519, 516; 607/9, 5

(56) References Cited

U.S. PATENT DOCUMENTS

| | | |
|---|---|---|
| 3,658,055 A | 4/1972 | Abe et al. |
| 5,836,889 A | 11/1998 | Wyborny et al. |
| 6,324,423 B1 * | 11/2001 | Callahan et al. |

FOREIGN PATENT DOCUMENTS

| | | |
|---|---|---|
| DE | 1 803 010 A1 | 1/1970 |
| DE | 196 09 411 A1 | 9/1997 |

* cited by examiner

Primary Examiner—Scott M. Getzow
(74) Attorney, Agent, or Firm—Venable, LLP.; Robert Kinberg

(57) ABSTRACT

A method for storing from a temporal sequence of a plurality of individual cardiac events cardiac rhythm information comprised of at least one determined type, in particular a sequence of time intervals between ventricular and/or atrial events, whereby a time interval continuum of the temporal distances between the events is subdivided into time portions of a predetermined length, which are each allocated a single-valuedd marker, in particular a number, each time interval detected with a detection of the cardiac rhythm as one recording is provided with the marker of the time portion into which it falls, the number of the recordings out of a predetermined total number of detected time intervals or belonging to each marker during a predetermined period of time, is assessed, and the markers which have been allocated from a predetermined number of time intervals or during a predetermined period of time at least one recording, each are stored along with the number of recordings.

16 Claims, 2 Drawing Sheets

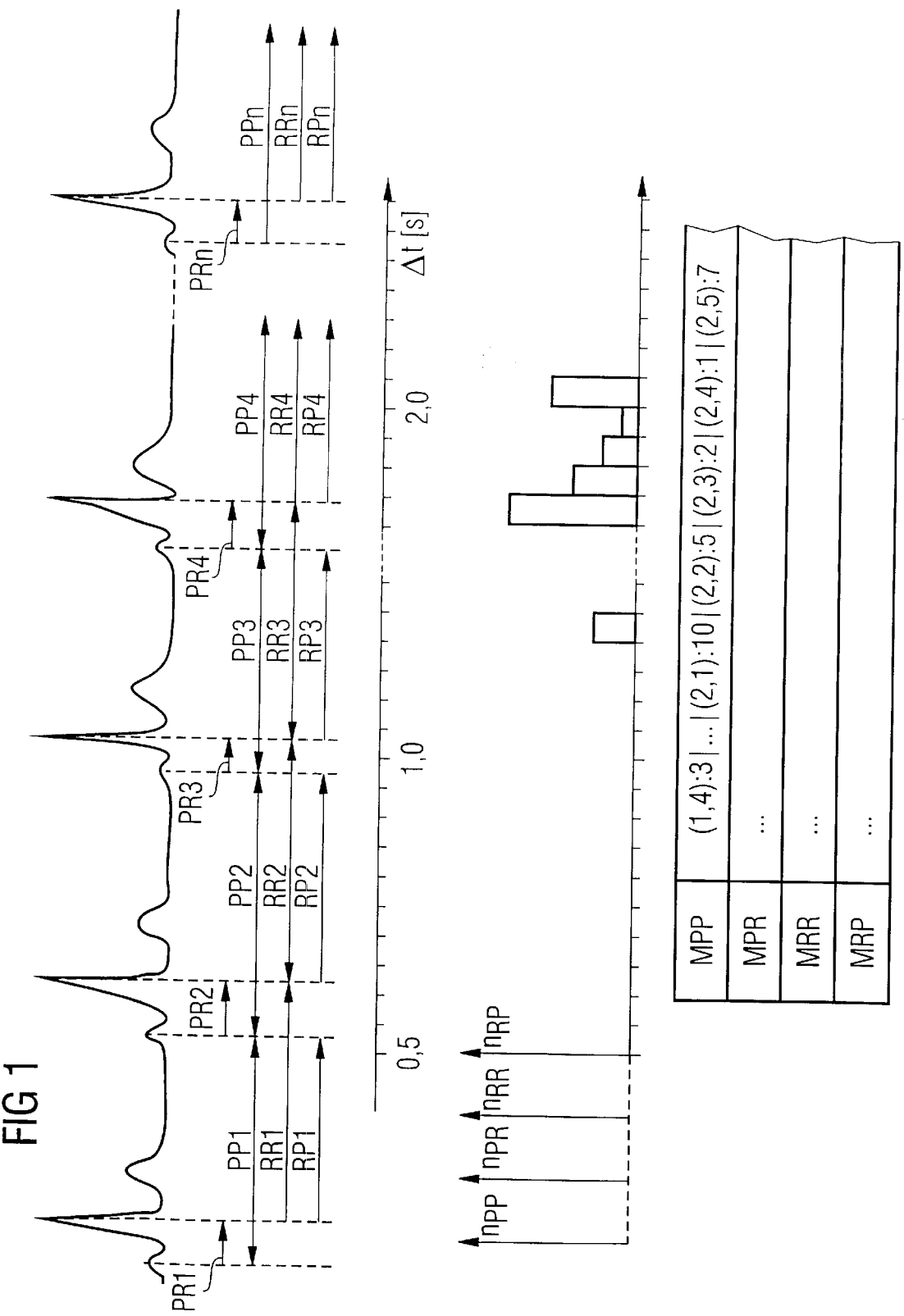

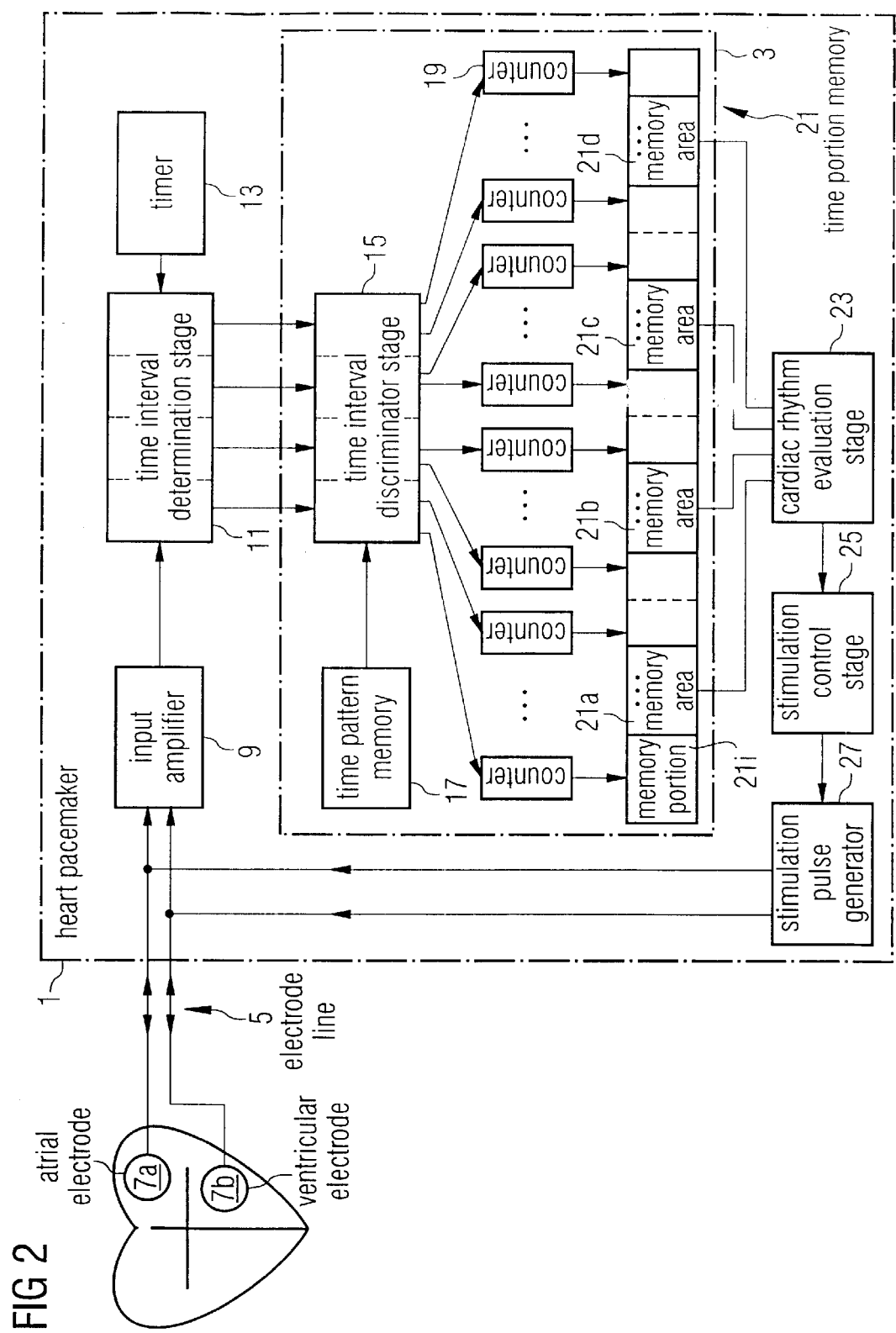

METHOD AND MEMORY MEANS FOR STORING CARDIAC RHYTHM INFORMATION

FIELD OF THE INVENTION

The invention relates to storing cardiac rhythm information.

BACKGROUND OF THE INVENTION

The most precise possible detection of cardiac rhythm information over sufficiently long periods of time and, if possible, in various physical and psychical situations of a patient, is—as has been known for a long time—an indispensable diagnostic aid for the cardiologist. In particular, monitoring of the temporal developments in the intervals between atrial events (the so-called PP intervals), as well as between ventricular actions(in particular the so-called RR intervals), as well as the time intervals between subsequent atrial and ventricular actions (of the PR intervals) or between ventricular and atrial actions (of the RP intervals), allows valuable conclusions as to specific arrythmiae.

Whereas in the out-patient and clinical practice of the cardiologist, the detection and recording of cardiac rhythm information is carried out, as a rule, by means of high-resolution ECG devices detecting as many details as possible so as to furnish to the physician valuable wave-shape data of the cardiac signals apart from the above-mentioned time intervals, the cardiac rhythm data detected on a patient over a certain period of time has to be processed and stored with a lowest possible expenditure in processing capacity and storage space for certain important applications. This requirement exists in particular with implanted cardiological devices which have been known and practically used for a prolonged period of time in the form of heart pacemakers for the treatment of bradycardia and/or tachycardia arrythmiae, as well as automatic defibrillators or cardioverters, or also as combined pacemakers/cardioverters or implanted drug dosing pumps.

Highly developed devices of this kind namely are equipped with one sensor or several sensors for detecting diagnostically relevant cardiac rhythm information in the patient's body, and with associated signal shaping and processing steps, as well as an evaluation and control unit making a selection between a number of pre-programmed operation parameters or therapy variants, and therapy parameters with dependence on the detected cardiac rhythm information, according to an algorithm stored in the device. In particular, stimulation devices count among these which are automatically activated or switched from one mode to another, depending on the detected cardiac state of the patient. Thus, with certain types of automatic implantable defibrillators and antitachycardia pacemakers, a continuous detection of the time intervals between atrial actions and/or ventricular actions is carried out over a sufficiently long period of time, so as to be able to recognize life-endangering acceleration of the cardiac rhythm as early as at its initial stage, and to respond thereto by means of an appropriate stimulation therapy.

So as to be able to reliably detect the mentioned life-endangering states (in particular atrial or ventricular fibrillation) in the various known signs of disease, on the occasion of which the mentioned automatic cardiac rhythm correction means are used, detection and storing must extend over a considerable period of time or a considerable number of cardiac actions.

Even when only the time intervals between the P and/or R waves of the heart signal are detected and stored, and the detection, processing and storage of wave-shape data is completely renounced of, a considerable processor and storage capacity will be required for this purpose in the implanted device. This is of less importance with respect to the costs of the processors and memory modules which, as a matter of course, become higher with increased capacity demand. Rather, it is of importance with respect to the power consumption and therewith, the lifetime of the battery. Despite considerable progress in primary cell technology and corresponding capacity enhancements of the lithium cells used in implanted devices, the power consumption for processing and storing the time intervals between heart actions leads to an essential decrease in the battery life, and therewith of the device lifetime in known heart pacemakers, Previously, several proposals have been made for compression methods which were specifically provided for a preprocessing of ECG information prior to processing or storing or, it general, for signal compression for implantable battery-operated devices.

Thus, in EP 0 263 599 A2, an ECG data compression is so proposed that a time marker is stored whenever the amplitude of the ECG input signal has changed by a certain amount as compared to the preceding recording date. In addition, art identification marker is stored upon a change of the sign of the increase of the ECG signal.

In EP 0 526 973 B1, the averaging for cardiac signals by means of a combined use of a temporal data compression and a sampling correlation is described, In U.S. Pat. No. 5,724,032, a method and an apparatus for compressing and displaying the cardiac rate within the scope of a fetal cardiac rhythm monitoring are described. This solution is based on the principle of the "maximum absolute difference", i.e. the data sampled within a certain interval are compared with an initial value, and the value having the highest absolute difference as compared to the initial value is selected and stored as a representation of the data sampled in said interval. This method is directed to a high degree of maintenance of highly frequent signal components which are valuable within the scope of clinical diagnosis.

In EP 0 540 144 B1, a method and an apparatus for ECG data compression are described, wherein the RR time intervals between subsequent ventricular actions along with sampling values obtained at certain intermediate moments of time are stored. Hereby, a reconstruction of the shape of the R waves becomes possible.

From the Applicant's DE 196 99 41 C2, a method and at device are known for storing signals in an implantable medical device, in particular for a compressed storing of ECG signal shape information. Hereby, the temporal signal course is sampled at predetermined time intervals and a subset of the sampling points is stored which is selected by means of a selection criterion—specifically the first differentiation of the temporal signal course as per time.

From EP 0 884 851 A2, a system and a method for data compression and for a non-linear sampling for implantable battery-operated devices are known which are also provided for an implantable pacemaker. The method resides essentially in the generation of a time-variable threshold value signal by means of which the physiological (analog) signal is compared with certain clock intervals. Hereby, a non-linear sampling is caused, and the thereby obtained data is finally subjected to a further compression.

From I. Provaznik, J. Kozumplik, "Wavelet transform in electrocardiography-data compression" Int. J. Med. Inf. 45

(1997), 111, an imaging diagnostic method on the basis of the Run-Length Encoding principle is known that is based on the decomposition of the ECG signal into a set of basic functions which completely cover the time-frequency domain. This method, as well as other, similar methods, is provided for ECG processing and recording in the outpatient and clinical area.

From U.S. Pat. No. 5,709,216, it is known to realize a data reduction of the measured values sampled in an implantable medical device by means of a method for variably resolving a data reduction, so as to reduce the storage space required. Hereby, for example, cardiac action intervals being physiological data, are converted into a digital value, whereby the digital representation is divided into portions, and individual subportions are allocated various resolution values.

From U.S. Pat. No. 5,819,740, a system and a method for compressing digitalized signals in implantable battery-fed devices are provided, by means of which especially an efficient telemetric transmission to an external receiver is supposed to be secured. In this solution, the method of determining a delta value or a difference between subsequent signal samples is used, whereby the largest of several determined delta values and the storage space required for the memorizing thereof is assessed, and the bit number and the herewith coded delta value are finally stored.

SUMMARY OF THE INVENTION

The invention is based on the object of providing an improved method which is simple and cost-efficient to implement, and an improved storage means of the generic kind, respectively, allowing for storing cardiac rhythm information with a significantly decreased expenditure in storage capacity and power consumption without an essential loss of information.

The above and other objects are accomplished in accordance with the invention by the provision of a method for storing from a temporal sequence of a plurality of individual cardiac events, cardiac rhythm information comprised of a sequence of time intervals between events of at least one of ventricular rhythm and atrial rhythm, comprising the steps of subdividing a time interval continuum of temporal distances between the events into time portions of a predetermined length, the time portions each being allocated a single-valued marker, the subdividing step ensuing in predetermined equal steps between 2 ms and 20 ms; providing each time interval detected along with a detection of the cardiac rhythm as one recording, with a marker of the time portion into which the time interval falls; assessing at least one of a number of recordings representing a count of recordings detected out of a predetermined total number of detected time intervals and a number of recordings representing a count of recordings belonging to each marker during a predetermined period of time; and storing the number of recordings and each of the markers which have been allocated from at least one of the recordings from the predetermined number of time intervals and the recordings during the predetermined period of time.

According to a second aspect of the present invention is provided a cardiac rhythm memory system comprising at least one memory means for storing detected cardiac rhythm information; at least one timing means for determining a storing period for the memory means; time interval discriminator means for allocating time intervals of the cardiac rhythm information detected within the storing period in each case to a plurality of predetermined, single-valued marked time portions, each time portion being subdivided into equal steps of between 2 ms and 20 ms; a plurality of recording counters corresponding to the plurality of the time portions for assessing a number of recordings representing a count of the recordings allocated to separate time portions during a storing period; and a plurality of memory portions corresponding to the plurality of time portions, each of said plurality of memory portions being allocated to one time position and being configured for storing the count of recordings.

According to a third aspect of the present invention is provided an implantable cardiac stimulation device for influencing the cardiac rhythm by means of electric stimulation pulses comprising a cardiac rhythm memory means including at least one memory means for storing detected cardiac rhythm information; at least one timing means for determining a storing period for the memory means; time interval discriminator means for allocating time intervals of the cardiac rhythm information detected within the storing period in each case to a plurality of predetermined, single-valued marked time portions; a plurality of recording counters corresponding to the plurality of the time portions for assessing a number of recordings representing a count of the recordings allocated to separate time portions during a storing period; and a plurality of memory portions corresponding to the plurality of time portions, each of said plurality of memory portions being allocated to one time position and being configured for storing the count of recordings.

The invention embraces the basic idea of storing the frequent occurrence of certain time interval values instead of each individual sampled time interval between certain cardiac actions—hence, of all of the RR or PP or PR or RP intervals sampled in a certain period of time. It may be observed that hereby, in particular with a high temporal constancy of the cardiac rhythm, high compression effects can be achieved. This advantage is particularly valuable when a detection and reasonable evaluation of an untimely atrial or ventricular action (PAC and/or PVC) within a stimulated, hence "rigid" cardiac rhythm is concerned.

The invention further embraces the idea that—contrary to the skilled person's current view—the information loss related to this data compression is uncritical for the use of the cardiac rhythm information. This applies with a good approximation to the above-mentioned application case of monitoring untimely contractions between stimulated cardiac actions.

Finally, the idea is a part of the invention to detect the mentioned time intervals according to a predetermined "patterning" of the time axis or (insofar as these were detected at a higher resolution), to allocate the detected values to such a pattern. By selecting the temporal resolution of the pattern, the compression rate can further be optimized with respect to the required information content of the cardiac rhythm information for a certain device function (e.g. triggering an antitachycardia stimulation or a cardioversion) For an essentially simultaneous (compressed) storage of various categories of time intervals, which must be distinguished from one another for the evaluation in the implantable device, one preferred embodiment of the method assigns in each case a single-valued category marker. Thus, expressed in a simplified manner, the time intervals between successive ventricular actions are assigned an "RR" marker, those occurring in the successive atrial actions are assigned a "PP" marker, the time intervals between an atrial and a subsequent ventricular action each are assigned a "PR" marker, and the intervals between a ventricular and a subsequent atrial action are assigned an "RP" marker. (It is understood that in the practical realization, digit values in a binary representation are used as the markers). Along with the inventive storing of the measured values allocated to portions of the selected time pattern, the category marker is then in each case carried along as well, and the counting of the recordings for the portions of the time pattern and the storing of the counted values ensues separately for the respective categories.

It is understood, however, that the method can be designed for certain types of cardiac rhythm correction devices, e.g. antibradycardia pacemakers or even certain defibrillators, to only detect a single type of cardiac events, and therewith to a single category of time intervals, thus allowing for dispensing of a category-related separate counting and storing. This fact simplifies the signal processing and storage, and hereby reduces the power required for this purpose, however, at the price of a reduced information content of the stored data.

The realization of the method ensues, such as has already been mentioned above, in a preferred manner by a combined time portion discrimination of the measured interval values relative to the predetermined time portions of the time pattern, and by an incrementation of a counter, which is allocated to that portion of the time pattern, into which the measured interval value was categorized. The term "time pattern" already implies that the division of the time continuum of the cardiac events into predetermined portions. Ls, preferably carried out with fixed steps. A part of a corresponding time pattern can, for example, comprise as time portions interval, lengths of . . . , 901–904 ms, 905–908 ms, 909–1002 ms, . . . , and hence is formed with a pattern pitch of 4 ms. It is understood that other pattern pitches, as well—determining the tolerance range for the evaluation of intervals as being corresponding intervals—can be used; from the present point of view, values in a range of between 2 ms and 20 ms are preferred.

From the present point of view, a method is of a particularly practical advantage, wherein pairs of RP and PR intervals are in each case recorded together, and are stored in pairs, whereby the category markers are carried along separately or an individual marker is allocated for the pair. This procedure is purposeful for the detection of the above-mentioned PVC or PAC within the scope of a stimulated cardiac rhythm.

According to the process aspects outlined above, a suitable memory means (in a broad interpretation of this term) exhibits time interval discriminator means for allocating the detected time intervals to portions of the time pattern, recording counters for the assessment of the recordings allocated to these time portions each in the storing period, and memory portions for recording the number of recordings. For determining the recording time interval a timer is provided. The latter interacts with a memory control in an appropriate manner so that the stored counted values allocated to the individual time portions are handled following the known FIFO storage principle.

Hence, with a continuous update of the storage count, in each case the oldest stored time interval value is to be cancelled, i.e. the count of the counter has to be decremented by 1 in that storage area, into which said interval value has entered. The realization of corresponding memory controls is within the scope of a skilled person's proceeding, and is therefore here not described in more detail.

The realization of the invention can largely be carried out in terms of software, so that the functional units mentioned in the preceding paragraph are not to be understood as hardware components. Thus, the entire storage content can be deposited as a data word or a data string in an unstructured memory in terms of hardware, whereby the counted values allocated to certain portions of the time pattern, are represented by bit groups at certain positions of the data string.

The detection of cardiac events as such, i.e. the extraction of the P or R points from the analog cardiac signal, is known to the person skilled in the art and is not the subject matter of the present invention, so that it will not be considered here in more detail. The detection of the temporal distance between these cardiac events—hence, the time intervals concerned here—is also within the skilled personas proceeding, and therefore does not require any description here.

Advantages and usefulness of the invention, incidentally, become clear from the subclaims and the subsequent description of a preferred embodiment by means of the Figures, wherein shows;

BRIEF DESCRIPTION OF THE DRAWINGS

FIG. 1 a graphical representation for illustrating a preferred realization of the proposed method, and FIG. 2 a schematic representation of components of a preferred memory means essential for the realization of the invention.

DETAILED DESCRIPTION OF THE INVENTION

In the upper part of FIG. 1, the temporal course of a cardiac signal is illustrated (in a strongly simplified manner) over a prolonged period of time embracing several heart beats. Below the drawing of the analog cardiac signal, the intervals are indicated which are characteristic for the cardiac rhythm, namely (a) the time intervals between two successive atrial actions (also referred to as atrial intervals; PP1 . . . PPm),
(b) the time intervals between successive ventricular actions (also referred to as ventricular intervals; RR1 . . . RRn),
(c) the time intervals between an atrial action and a subsequent ventricular action (also referred to as atrial-ventricular intervals; PR1 . . . PRm), and
(d) the time intervals between ventricular actions and subsequent atrial actions (also referred to as ventricular-atrial intervals; RP1 . . . RPn), Below this part of FIG. 1, a time scale with relevant time portions is shown, under which these characteristic time intervals of the cardiac signal typically fall. Here, each time portion can be centered around a scale graduation mark, hence, for example, reaching from 925 ms to 975 ms, or can, on the other hand, extend between two scale graduation marks, hence, for example, reaching from 900 ms to 950 ms. The illustrated example (wherein the pattern pitch, as compared to usually existing practical requirements, is slightly too coarse), proceeds from an equidistant division of the time axis. The time axis, however, can also be subdivided in portions of unequal lengths. It would, for example, be sensible to subdivide the cardiac rhythm into frequency portions of the same width—since in this case, the formation of the reciprocal value would lead to an unequal pattern pitch of the time axis.

Below the time axis represented as a pattern, it is symbolically shown by means of four ordinates placed one beside the other and a common abscissa, that the number (outlined as ordinate) of the recordings associated to each time portion of the course of the cardiac signal under evaluation is allocated in each case to the time portions— and namely separately for each category of time intervals. The represented distribution of the frequent occurrence is selected in a merely arbitrary manner.

At the very bottom, it is—again symbolically—illustrated how the time portions covered during the determination of the time intervals, in each case including the number of the associated recordings, are stored in separate memory areas MPP, MPR, MRR and MRP. These memory contents constitute the data base relevant for the diagnostic function of an implantable cardiac rhythm correction device. Said data base is employed continuously according to a pre-programmed evaluation algorithm for obtaining a control signal for the device concerned, which controls in particular the maintenance of the stand-by mode or the actuation of an electrostimulating therapy in the case of a distribution of the relevant time intervals which has to be classified as being dangerous.

In FIG. 2, as an essential component of an implantable heart pacemaker 1 in conjunction with the invention, a time interval memory means 3 in its functional structure and its interaction with the input and the output of components adjacent to the output side of a pacemaker is illustrated. The structure of a pacemaker is presupposed as being known, and is therefore neither shown nor explained in the Figure.

The heart pacemaker 1 is connected to an atrial electrode 7a and a ventricular electrode 7b via an electrode line 5, and receives a cardiac signal from there, which is processed in an amplifier stage 9 by means of filter and amplifier stages, and is conveyed to a time interval determination stage 11 in communication with a timer 13. In the time interval determination stage 11, the above-mentioned time intervals of the cardiac rhythm, hence the PP, the RR, the PR and the RP interval, are assessed with an accuracy determined by the accuracy of the timer 13 from the (analog) processed input signals by means of methods of signal analysis known per se. (In practice, the arrangement outlined here will be configured multichannel—such an arrangement is, however, known and apart therefrom, does not concern the invention, so that a detailed explanation can be dispensed of in this place) The time interval determination stage 11 outputs the detected PP, RR, PR and RP intervals via four outputs.

The outputs of the time interval determination stage 11 each are connected to one input of the time interval discriminator, stage 15 which is in communication with a programmable time pattern memory 17 via a control input. In this memory (according to the second partial illustration from above in FIG. 1), a time pattern is stored prior to the categorization of the measured time intervals, said time pattern being applied in the time interval discriminator stage 15. The time interval discriminator stage 15, comprises a plurality of outputs for each "channel", i.e. a processing area in each case connected to an input; which outputs are each allocated to one of the pre-programmed time portions. Upon recording a time interval falling into the corresponding time portion, a signal is outputted at the corresponding output, incrementing a thereto connected counter 19. The counters 19 are connected to a memory portion 21i of the time portion memory 21 which comprises four memory portions 21a, 21b, 21c and 21d for the separate storage of the distribution of the frequent occurrence of the PP, RR, PR and RP intervals.

On the output side, the time portion memory 21 is connected to a cardiac rhythm evaluation stage 23, in which, according to a pre-programmed evaluation algorithm and, if the case should be, under recourse to other parameters, the assessed and stored distribution of the relevant time intervals of the patient's cardiac rhythm is evaluated. Finally, the cardiac rhythm evaluation stage 23 is connected to a stimulation control stage 25, which drives a stimulation pulse generator 27 according to a likewise pre-programmed stimulation pulse therapy for transmitting stimulation pulses via the electrode line 5 to the atrial electrode 7a and/or the ventricular electrode 7b. The dependence of certain stimulation therapies on a determined distribution of relevant time intervals of cardiac rhythm is not the subject matter of the invention; in this respect extensive prior art exists, which is known to the person skilled in the art, and which can be used with the realization of the invention.

The realization of the invention is not restricted to the aspects pointed out above and the explained embodiment, which is meant only for the purpose of a schematic illustration, but is also possible in a plurality of modifications which are within the skilled person's proceeding.

LIST OF REFERENCE NUMERALS 1 heart pacemaker
3 interval memory means
5 electrode line
7a atrial electrode
7b ventricular electrode
9 input amplifier
11 time interval determination stage
13 timer
15 time interval discriminator stage
17 time pattern memory
19 counter
21 time portion memory
21a, 21b, 21c 21d memory area
21i memory portion
23 cardiac rhythm evaluation stage
25 stimulation control stage
27 stimulation pulse generator,

What is claimed is:

1. A method for storing from a temporal sequence of a plurality of individual cardiac events, cardiac rhythm information comprised of a sequence of time intervals between events of at least one of ventricular rhythm and atrial rhythm, comprising the steps of:

subdividing a time interval continuum of temporal distances between the events into time portions of a predetermined length, the time portions each being allocated a single-valued marker, the subdividing step ensuing in predetermined equal steps between 2 ms and 20 ms;

providing each time interval detected along with a detection of the cardiac rhythm as one recording, with the marker of the time portion into which the time interval falls;

assessing at least one of a number of recordings representing a count of recordings detected out of a predetermined total number of detected time intervals and a number of recordings representing a count of recordings belonging to each marker during a predetermined period of time; and storing the markers which have been allocated at least one recording, whereby the markers have been allocated at least of (a) from a predetermined number of time intervals, and (b) during a predetermined period of time, each marker being stored along with the number of recordings.

2. The method according to claim 1, wherein the single-valued marker is a number.

3. The method according to claim 1, wherein the subdividing step ensues in equal steps of 4 ms.

4. The method according to claim 1, further comprising the steps of:
    allocating a single-valued category marker to each of a plurality of categories of time intervals, representing various time intervals between cardiac events;
    storing the category marker along with the single-valued marker of the time portion into which a respective time interval falls; and
    counting the recordings belonging to said time portions in a category-related manner.

5. The method according to claim 1, further comprising the steps of:
    detecting time intervals for at least one of the ventricular and atrial rhythms, including at least one of (a) RR intervals between two successive ventricular rhythms; (b) PP intervals between two successive atrial rhythms; (c) PR intervals between successive atrial and ventricular rhythms; and (d) RP intervals between ventricular and atrial rhythms; and
    storing in a category-related manner the allocated markers of the respective time portions for at least one of the time intervals.

6. The method according to claim 1, wherein the assessing step includes the steps of:
    calculating a temporal distance to a previously detected cardiac event;
    discriminating a time portion relative to the predetermined time portions; and
    incrementing a counter which is allocated to the time portion recognized as being a valid result according to a result of the discriminating step.

7. The method according to claim 1, wherein natural and stimulated cardiac events are subjected to a common recording and storing process.

8. A cardiac rhythm memory system comprising:
    at least one memory means for storing detected cardiac rhythm information;
    at least one timing means for determining a storing period for the memory means; time interval discriminator means for allocating time intervals of the cardiac rhythm information detected within the storing period in each case to a plurality of predetermined, single-valued marked time portions, each time portion being subdivided into equal steps of between 2 ms and 20 ms;
    a plurality of recording counters corresponding to the plurality of the time portions for assessing a number of recordings representing a count of the recordings allocated to separate time portions during the storing period; and
    a plurality of memory portions corresponding to the plurality of time portions, each of said plurality of memory portions being allocated to one time portion and being configured for storing the count of recordings.

9. The cardiac rhythm memory system according to claim 8, further comprising a plurality of groups of memory areas, each group being single-valued and being allocated to a respective category of time intervals, and comprising a plurality of memory areas each for one predetermined time portion within the respective category.

10. A method for storing from a temporal sequence of a plurality of individual cardiac events cardiac rhythm information comprised of a sequence of time intervals between events of at least one of ventricular rhythm and atrial rhythm, comprising the steps of:
    subdividing a time interval continuum of the temporal distances between the events into time portions of a predetermined length, each time portion being allocated a single-valued marker, the marker being a number;
    providing each time interval detected along with a detection of the cardiac rhythm as one recording, with the marker of the time portion into which it falls;
    assessing at least one of (a) a number of recordings representing a count of recordings detected out of a predetermined total number of detected time intervals, and (b) a number of recordings representing a count of recordings belonging to each marker during a predetermined period of time; and
    storing the markers which have been allocated at least one recording, whereby the markers have been allocated at least one of (a) from a predetermined number of time intervals, and (b) during a predetermined period of time, each marker being stored along with the number of recordings;
    detecting, for at least one of ventricular and atrial events, at least one of (a) RR intervals between two successive ventricular events, (b) PP intervals between two successive atrial events; (c) PR intervals between successive atrial and ventricular events, (d) and RP intervals between successive ventricular and atrial events, wherein said RP intervals and PR intervals each are detected in pairs; and
    storing the markers of respective time portions for various categories of time intervals in a category-related manner, wherein the markers for the RP and PR intervals are at least one of (a) stored in pairs and (b) combined in a common marker for the pair in a category-related manner.

11. The method according to claim 10, wherein the subdividing step ensues in equal steps of 4 ms.

12. The method according to claim 10, further comprising the steps of:
    allocating a single-valued category marker to each of a plurality of categories of time intervals, representing various time intervals between cardiac events;
    storing the category marker along with the single-valued marker of the time portion into which a respective time interval falls; and
    counting the recordings belonging to said time portions in a category-related manner.

13. The method according to claim 10, wherein the assessing step includes the steps of:
    calculating a temporal distance to a previously detected cardiac event;
    discriminating a time portion relative to the predetermined time portions; and
    incrementing a counter which is allocated to the time portion recognized as being a valid result according to a result of the discriminating step.

14. The method according to claim 10, wherein natural and stimulated cardiac events are subjected to a common recording and storing process.

15. An implantable cardiac stimulation device for influencing the cardiac rhythm by means of electric stimulation pulses comprising a cardiac rhythm memory means including:
    at least one memory means for storing detected cardiac rhythm information;
    at least one timing means for determining a storing period for the memory means;

time interval discriminator means for allocating time intervals of the cardiac rhythm information detected within the storing period in each case to a plurality of predetermined, single-valued marked time portions;

a plurality of recording counters corresponding to the plurality of the time portions for assessing a number of recordings representing a count of the recordings allocated to separate time portions during the storing period; and a plurality of memory portions corresponding to the plurality of time portions, each of said plurality of memory portions being allocated to one time portion and being configured for storing the count of recordings.

16. The implantable cardiac stimulation device according to claim 15, wherein the device comprises at least one of a pacemaker and a defibrillator.

* * * * *